United States Patent [19]

Scott

[11] Patent Number: 5,045,559

[45] Date of Patent: Sep. 3, 1991

[54] TREATMENT OF SKIN DISORDERS

[75] Inventor: Ian R. Scott, Wellingborough, England

[73] Assignee: Unilever Patent Holdings B.V., Vlaardingen, Netherlands

[21] Appl. No.: 351,749

[22] Filed: May 15, 1989

[30] Foreign Application Priority Data

May 13, 1988 [GB] United Kingdom ............. 8811410.3

[51] Int. Cl.$^5$ .............................................. A61K 31/40
[52] U.S. Cl. ..................................... 514/423; 514/852; 514/859; 514/861; 514/863; 514/864
[58] Field of Search ............... 514/423, 852, 859, 861, 514/863, 864

[56] References Cited

U.S. PATENT DOCUMENTS

| 3,235,457 | 2/1966 | Laden | 514/423 X |
| 3,836,665 | 9/1974 | Eberhardt et al. | 514/423 |
| 4,772,601 | 9/1988 | Martin | 514/423 X |
| 4,774,255 | 9/1988 | Black et al. | 514/423 |

FOREIGN PATENT DOCUMENTS 57-185209 11/1982 Japan .
60-214744 10/1985 Japan .

Primary Examiner—Leonard Schenkman
Attorney, Agent, or Firm—Cushman, Darby & Cushman

[57] ABSTRACT

A therapeutic composition for the treatment of skin disorders comprises a therapeutically effective amount of a curative agent chosen from special esters of pyroglutamic acid, and mixtures thereof, in a therapeutically acceptable vehicle for topical application.

7 Claims, No Drawings

TREATMENT OF SKIN DISORDERS

FIELD OF INVENTION

The invention relates to a therapeutic composition and its use in the treatment or prevention of certain skin disorders, and more particularly to the use of certain esters of pyroglutamic acid, in the preparation of therapeutic compositions for the treament or prevention of specified skin disorders.

The therapeutic composition is intended for topical application to human skin, particularly to treat skin disorders such as ichthyotic dermatoses, hyperkeratosis and related conditions.

BACKGROUND & PRIOR ART

The conventional treatment of skin disorders such as ichthyotic dermatoses, hyperkeratosis and related conditions has included topical application to the affected area of skin of ointments, creams, lotions or powders containing one or more of a wide variety of active ingredients such as organic and inorganic acids, steroids, fungicides, antibiotics and anti-inflammatory substances.

Usually, remission of the disorder is slow and frequently incomplete. Complete remission and cure of some skin conditions can usually only be obtained by the use of potent drugs, such as steroids, having often severe contra indications which limit their widespread use without medical supervision. Also, the topical application of caustic chemicals in the treatment of localised conditions, such as warts, is often accompanied by pain or discomfort which also limits their use.

It has been suggested in the clinical literature that certain skin disorders are due to insufficient acidity in the epidermal acid layer or coat of the skin. Accordingly, certain skin conditions including one reported case of ichthyosis were apparently successfully treated by lowering the pH of the patient's acid coat. The treatment included topical application of a 3% buffered lactic acid-containing cream.

The use of certain esters of pyroglutamic acid as auxiliary agents for accelerating absorption of drugs through the skin is described in JA 60-214 744 (Nitto Denki Kogyo KK). No curative benefit for the esters per se is mentioned.

Cosmetics containing one or more compositions obtained by the esterification of 2-pyrrolidone-5-carboxylic acid (PCA) and a fatty acid chosen from straight chain higher fatty acid are described in JA 57-185209 (Nisshin Seiyu KK). These are described as novel oily materials for cosmetic use. There is no suggestion that these materials could have any curative benefit in the treatment of skin disorders.

It has now been discovered that certain skin disorders may be treated successfully to at least reduce their symptoms, by topical application of a safe, effective curative agent chosen from certain esters of pyroglutamic acid. These esters are free from the contra indications associated with the topical applications of certain drugs.

Mode of Action of the Esters

Pyroglutamic acid (also known as 2-pyrrolidone-5-carboxylic acid) is the principal ingredient of the "natural moisturising factor" that enables the stratum corneum of the skin to maintain a high water content despite low external humidity. Pyroglutamic acid applied topically to the skin has a temporary moisturising effect but it is easily washed away and gives no long term skin benefit.

The esters of pyroglutamic acid according to the invention are substrates for stratum corneum enzymes. It has been discovered that these esters readily penetrate into the stratum corneum, and there provide a substrate for these enzymes at the normal site of pyroglutamic acid synthesis, that is, inside the cells of the stratum corneum.

The amount of pyroglutamic acid produced naturally in the stratum corneum is strictly limited by the amount of a preformed protein precursor accumulated by the stratum corneum cell while it is undergoing development (see: I R Scott, C R Harding & J G Barrett [1982] "Histidine-rich protein of the keratohyalin granules : source of free amino acids, urocanic acid and pyrrolidone carboxylic acid in the stratum corneum". Biochim. Biophys-Acta 719, 110). Treatment of the skin with the esters according to the invention can therefore enable the skin to produce, using its own synthetic machinery, higher levels of pyroglutamic acid than would otherwise be possible.

Because pyroglutamic acid is thereby produced within the cells of the stratum corneum, it is very resistant to removal by washing, a significant fraction remaining after a continuous 2 hour period of water washing. This is particularly important in the treatment of dry skin, symptomatic of many skin disorders.

Accordingly, it has been discovered that compositions containing esters of pyroglutamic acid, as herein defined, cause the pyroglutamic acid content of skin to increase, alleviate skin dryness, improving skin smoothness and generally bring about a remission of skin disorders, especially those characterised by skin dryness and flaking. Also, we have found that the ester of pyroglutamic acid penetrates more readily into the stratum corneum than does the free acid, the penetrated ester being enzymically cleaved as already stated, to yield pyroglutamic acid in situ in the stratum corneum, thereby to augment that which occurs naturally in this region of the skin. Evidence to support this observation is given later in this specification.

It is also apparent that the intact esters of pyroglutamic acid, as herein defined, have a direct benefit on the remission of certain specified skin disorders.

DEFINITION OF THE INVENTION

Accordingly, the invention provides for the use of a curative agent chosen from esters of pyroglutamic acid and mixtures thereof, in the preparation of a therapeutic composition for the treatment of the skin disorders:
Ichthyosiform dermatoses, notably:
Ichthyosis vulgaris,
Sex-linked ichthyosis,
Lamellar ichthyosis,
Epidermolytic ichthyosis,
Conradi's syndrome
Localised hyperkeratotic conditions, notably:
Keratosis pilaris,
Keratosis punctata,
Keratosis senilis,
Keratosis striata,
Dandruff
Callous-forming disorders, notably:
Palmar and Plantar hyperkeratosis, including corns,
Palmar and Plantar keratoderma, Psoriasis,
Eczema,
Xerosis,
Warts notably
Keratotic warts,
Herpes,
Keratoacanthoma,
Warty naevus,
Tinea pedis and other dermatomycoses,
Pityriasis rosea & Pityriasis alba,
Lichen planus & Lichen simplex chronicus,
Cicatricial alopecia with dry flaky scalp,
Darier's disease,
Pruritus,
Seborrhoeic dermatitis,
Seborrhoeic eczema,
Acne,
Scabies;
the esters of pyroglutamic acid having the structure:

$$\begin{array}{c} O = \underset{\underset{H}{|}}{N} \\ \end{array} \underset{\underset{O}{\|}}{C} - O - R \quad (1)$$

where
R is a linear or branched chain, saturated or unsaturated alkyl group having from 1 to 30 carbon atoms, or the group:

$$\begin{array}{c} R' \quad O \\ | \quad \| \\ -CH-C-OR'' \end{array}$$

where
R' and R'' are the same or different and are each represented by H or the group:

$$[(CH_3)_u(CH_2OH)_v(CH_2)_w(CHCH_3)_x(CHOH)_y(CH=CH)_z]- \quad (2)$$

where
u is zero, or 1
v is zero, or 1
w is zero, or an integer of from 1 to 21
x is zero, or an integer of from 1 to 4
y is zero, or an integer of from 1 to 2
z is zero, or an integer of from 1 to 4; and
$u+v+w+x+y+z$ is an integer of from 1 to 22;
the subgroups within the group (2) being in any sequence; provided that when the subgroup (CH=CH) is present, then the total number of carbon atoms in said group (2) will be from 10 to 22.

The invention also provides a therapeutic composition for the treatment of skin disorders as herein defined which composition comprises a therapeutically effective amount of a curative agent chosen from esters of pyroglutamic acid and mixtures thereof, as herein defined, in a therapeutically acceptable vehicle for topical application.

The invention also provides a method for the treatment of skin disorders, as herein defined, comprising topically applying to involved areas of the body an effective amount of a composition comprising as an active ingredient, a curative agent chosen from esters of pyroglutamic acid esters and mixtures thereof, as herein defined, in a therapeutically acceptable vehicle for topical application.

The invention also provides for the use of a therapeutic composition comprising as an active ingredient, a curative agent chosen from esters of pyroglutamic acid and mixture thereof, as herein defined, in the treatment or prevention of skin disorders, as herein defined.

DISCLOSURE OF THE INVENTION

It is accordingly an object of the invention to provide a therapeutic composition containing as a curative agent, one or more esters of pyroglutamic acid, which when applied topically to the skin of a person suffering from one or more of the skin disorders, as herein defined, will alleviate and/or effect remission of the symptoms of the disorder(s).

The esters of pyroglutamic acid

Examples of suitable esters of pyroglutamic acid where R in structure (1) is a $C_1$ to $C_{30}$ linear or branched chain alkyl group, as curative agents for use in the preparation of the therapeutic composition according the invention, are:
pyroglutamic acid methyl ester
pyroglutamic acid ethyl ester
pyroglutamic acid n-propyl ester
pyroglutamic acid n-butyl ester
pyroglutamic acid n-hexyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradecyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimethyl-1-pentane ester
pyroglutamic acid methyloctyl ester.

Particularly preferred esters of this group are those where R in structure (1) is $C_1$ to $C_{14}$ alkyl, (linear or ranched), especially $C_1$ to $C_6$ alkyl (linear or branched).

Examples of the group (2) include straight and branched chain, saturated or unsaturated aliphatic groups having from 1 to 22 carbon atoms, such as the alkyl groups:
methyl
ethyl
propyl
iso-propyl
butyl
iso-butyl
n-valeryl
iso-valeryl
n-caproyl
n-heptyl
n-caprylyl
n-capryl
lauryl
myristyl palmityl
stearyl
arachidyl, and
behenyl;
and the $C_{10-22}$ alkenyl groups:
linoleyl
linolenyl
γ-linolenyl
arachidonyl, and
columbinyl.

Examples of the group (2) also include hydroxyalkyl groups having from 1 to 22 carbon atoms, such as:
hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

Further specific examples of esters of pyroglutamic acid containing the grouping

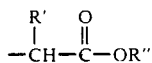

are:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-perlargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

It is to be understood that the above list of specific examples of esters of pyroglutamic acid are not exhaustive, there being many other examples expressed by the generic structure of these esters.

The amount of the esters of pyroglutamic acid or mixtures thereof to be employed in accordance with the invention, as a therapeutically effective amount, will normally be from 0.01 to 20%, preferably from 0.1 to 10% and most preferably from 0.2 to 2% by weight of the therapeutic composition.

Therapeutically acceptable vehicle

The therapeutic composition of the invention also comprises a therapeutically acceptable vehicle, usually in the form of a lotion, cream, ointment, gel, powder, solid stick or aerosol concentrate formed from cosmetically acceptable ingredients as conventionally employed in the art.

The amount of the therapeutically acceptable vehicle to be employed in accordance with the invention will normally form the balance of the therapeutic composition after taking account of the ester of pyroglutamic acid or a mixture thereof, and optional ingredients. Accordingly, the therapeutically acceptable vehicle with normally form from 50 to 99.89%, preferably from 70 to 99.4% by weight of the therapeutic composition.

OPTIONAL INGREDIENTS

The therapeutic composition according to the invention can also optionally contain further ingredients in addition to those which are conventionally used for the provision of the therapeutically acceptable vehicle.

Accordingly, in addition to ingredients conventionally used in preparing a lotion, cream, ointment, gel, powder, solid stick and aerosol concentrate, the therapeutic composition can optionally comprise further ingredients such as a perfume, colourant, preservative, antioxidant, emollient or aerosol propellant, and activity enhancers in amounts which are conventional in the cosmetics or pharmaceutical art.

PREPARATION OF THE THERAPEUTIC COMPOSITION

The therapeutic composition of the invention can be prepared in the form of a solution, lotion, gel, cream, ointment, solid stick, aerosol or powder, or in any other form suited to administration topically to human skin.

When the therapeutic composition is a liquid, such as a lotion or aerosol, or a semi-liquid such as a gel, cream or ointment, or a solid stick, then it is usually necessary to dissolve an effective quantity of the ester of pyroglutamic acid, or a mixture thereof, in water or ethanol or other aqueous or non-aqueous therapeutically acceptable vehicle, and then to admix this solution, if desired, in a conventional manner with a suitable cream or ointment base containing, for example an oil or silicone oil and water, or stick base containing a gelling agent such as sodium stearate, or with a normally liquefiable gaseous propellant in order to prepare the therapeutic composition.

When the therapeutic composition is a powder, then it is usually necessary to admix the ester of pyroglutamic acid or a mixture thereof, with a powder diluent, such as talc, starch, kaolin, Fuller's earth or other suitable powder base, in order to provide the therapeutic composition in powder form.

If desired, other therapeutically acceptable carriers, diluents or emollients can be incorporated in the therapeutic composition according to the invention, in order to facilitate even distribution over the affected area of the skin at a concentration or dosage suitable for treatment or prevention of the skin disorder, as herein defined.

It is also possible to incorporate in the therapeutic composition according to the invention other therapeutic active substances which may further improve the treatment of skin disorders.

Adjustment of pH

When the therapeutic composition contains water, then the aqueous phase should have a pH value of from 2 to 9, preferably from 3 to 7 and ideally from 4 to 6.

Although therapeutic compositions having a pH value of less than 2 are likely to be effective in the treatment skin disorders, as herein defined, topical application of such compositions can occasionally produce stinging, burning or irritation, particularly when the skin is broken, cut or otherwise damaged. Therapeutic compositions having a pH value of greater than 9 are likely to exhibit reduced effectiveness in the treatment of skin disorders, due to instability of the ester above pH 9. Evidence in support of establishing a preferred pH value of from 3 to 7 to maximise stability of the ester of pyroglutamic acid is given later in this specification.

Any suitable therapeutically acceptable pH adjustant can be employed to set the pH of the composition at a desired value. Examples of pH adjustants include alkanolamines, especially triethanolamine and buffers such as lactic acid/triethanolamine lactate.

METHOD OF TREATMENT

The invention also provides a method for the treatment of skin disorders in man and other mammals, namely:

Ichthyosiform dermatoses, notably:
Ichthyosis vulgaris,
Sex-linked ichthyosis,
Lamellar ichthyosis,
Epidermolytic ichthyosis,
Conradi's syndrome,
Localised hyperkeratotic conditions, notably:
Keratosis pilaris,
Keratosis punctata,
Keratosis senilis,
Keratosis striata,
Dandruff,
Callous-forming disorders, notably:
Palmar and Plantar hyperkeratosis, including corns,
Palmar and Plantar keratoderma,
Psoriasis,
Eczema,
Xerosis,
Warts, notably:
Keratotic warts,
Herpes,
Keratoacanthoma,
Warty naevus,
Tinea pedis and other dermatomycoses,
Pityriasis rosea & Pityriasis alba,
Lichen planus & Lichen simplex chronicus,
Cicatricial alopecia with dry flaky scalp,
Darier's disease,
Pruritus,
Seborrhoeic dermatitis,
Seborrhoeic eczema,
Acne,
Scabies, which method of treatment comprises applying to involved areas of the body an effective amount of a composition comprising from 0.01 to 20% by weight of a curative agent chosen from esters of pyroglutamic acid, as herein defined, or mixtures thereof, together with a therapeutically acceptable vehicle.

In vitro evidence to confirm delivery of pyroglutamic acid to stratum corneum of the rat In an in vitro laboratory test, esters of pyroglutamic acid labelled with $^3H$ on the pyroglutamic acid residue were applied as a 1% by weight solution in ethanol to newborn rat skin held in a glass cell, allowing the dermal side of the skin to be bathed in a buffered salts solution while the epidermal surface was exposed to normal atmospheric conditions. After 24 hours, samples of skin were taken and washed with continuous agitation in several charges of water at room temperature.

Interfollicular epidermis was removed from these skin pieces by "freeze scraping"-which avoids contamination of the sample by follicular tissue or material trapped within the hair follicle. The epidermis was then extracted in methanol and the soluble extract analysed by column chromatography. The amount of tritiated pyroglutamic acid present in the epidermis in a form resistant to a period of 2 hours continuous washing with water was measured. The quantity of tritiated pyroglutamic acid delivered and retained by the skin in this way is recorded in Table 1 below:

TABLE 1

| Ester | Pyroglutamic acid delivered (n moles/cm$^2$ skin) |
|---|---|
| Pyroglutamic acid, methyl ester | 17 ± 5 |
| Pyroglutamic acid, ethyl ester | 18 ± 5 |
| Pyroglutamic acid, n-propyl ester | 21 ± 8 |
| Pyroglutamic acid, n-butyl ester | 17 ± 8 |
| Pyroglutamic acid, n-hexyl ester | 32 ± 10 |
| Pyroglutamic acid, n-octyl ester | 36 ± 7 |

These results indicate that topical application of each of these esters of pyroglutamic acid resulted in delivery to the stratum corneum of substantial quantities of pyroglutamic acid which resisted washing out with water. It is to be noted that the n-octyl ester of pyroglutamic acid give the best result in this respect.

In vivo evidence to support benefit of topical application to human skin of the ester of pyroglutamic acid versus the free acid When pyroglutamic acid is applied topically to human skin, only a negligible amount is able to penetrate to the stratum corneum to augment that naturally present in this region of the skin. However, certain esters of pyroglutamic acid are able readily to penetrate the skin to reach the stratum corneum, where naturally occurring esterases cleave the ester to yield the free pyroglutamic acid which can then augment that which is naturally present in the skin, with the consequence that skin benefit is improved.

Delivery of esters of pyroglutamic acid, with subsequent hydrolysis to yield free pyroglutamic acid in the stratum corneum, was confirmed using tritiated esters of pyroglutamic acid and a radio-tracer technique.

Accordingly, [$^3H$] esters of pyroglutamic acid were each dissolved at 1% w/v in anhydrous ethanol or in an oil-in-water emulsion base. These solutions were then applied to the arms of volunteers, left for 18 hours, washed with soap and water, and the stratum corneum was removed by stripping with Sellotape. The [$^3H$] pyroglutamic acid was separated from unchanged ester by chromotography on AG1X8 resin and the amount delivered to the skin expressed as nmoles per mg of stratum corneum protein.

The result obtained are summarised in Table 2:

TABLE 2

| Ester of Pyroglutamic acid | Pyroglutamic acid delivered (n mol/mg protein) | |
| --- | --- | --- |
| | Ethanol base | Cream base |
| Ethyl | 8 | 5 |
| Butyl | 6 | 2 |
| Hexyl | 5 | 2 |
| Octyl | 4 | 1 |
| Dodecyl | 4 | 1 |

When [$^3$H] pyroglutamic acid instead of a corresponding ester was applied topically in this experiment, a negligible amount of the tritiated free acid was recovered from the stratum corneum.

The above results (Table 2) indicate that pyroglutamic acid is effectively delivered to the stratum corneum following topical application of an ester thereof, while little pyroglutamic acid reached the stratum corneum if applied as the free acid. These results also indicate a preference for an anhydrous ethanolic composition, rather than an aqueous cream base. Also, the shorter the alkyl chain of the ester, the more effective the delivery of the ester to the stratum corneum, as judged by the higher yield of pyroglutamic acid found in that region of the skin.

Evidence to support preference for acid pH value of composition for improved stability of the ester of pyroglutamic acid As has been stated earlier, the stability of the ester of pyroglutamic acid during storage prior to use is improved in compositions having an acid pH, compared with those having a neutral or alkaline pH. It is accordingly apparent that hydrolysis of the ester with premature release of free pyroglutamic acid can occur faster at higher pH values than at lower values. Compositions having maximum skin benefit are therefore those having a pH value of <7 containing the unchanged ester of pyroglutamic acid with minimal free pyroglutamic acid, although a pH value of up to 9 can be acceptable particularly where a long shelf life of several months or up to 1 year is not essential.

In order to demonstrate the effect of pH on the stability of esters of pyroglutamic acid, the half-life of selected esters at selected pH values was measured as follows:

i) The chosen ester of pyroglutamic acid was dissolved in aqueous buffer of a selected pH value, to provide a 0.1% w/v solution of the ester;

ii) Intact (unhydrolysed) ester was analysed by high performance liquid chromatography at regular time intervals.

iii) The log of the amount of the ester remaining intact versus time was plotted to give a straight line response.

iv) From this plot, the time required for half of the ester of pyroglutamic acid to be hydrolysed (half of the ester remaining intact), can be determined if necessary by extrapolation.

Using this method, the half-life of selected esters of pyroglutamic acid was determined and the results obtained were as follows:

TABLE 3

STABILITY OF VARIOUS ALKYL ESTERS OF PYROGLUTAMIC ACID*

| ESTER | HALF LIFE IN HOURS | |
| --- | --- | --- |
| | pH 7.0 | pH 4.0 |
| Ethyl-2-[pyroglutamoyloxy]-n-propionate | 9 | 1,700 |
| Pyroglutamic acid ethyl ester | 58 | 11,000 |
| Pyroglutamic acid n-butyl ester | 80 | 15,000 |
| Pyroglutamic acid n-hexyl ester | 96 | 18,000 |
| Pyroglutamic acid n-octyl ester | 96 | 18,000 |

*Assay performed in 100 mM phosphate buffer at 30° C.

The half-life of pyroglutamic acid ethyl ester was also determined over a narrower range of pH values on either side of neutrality to illustrate the preference for selecting a pH value for improved stability of <7.

TABLE 4

STABILITY OF PYROGLUTAMIC ACID ETHYL ESTER AT pH VALUES NEAR NEUTRALITY

| pH value | Half-life (days) |
| --- | --- |
| 6.5 | 12 |
| 6.8 | 7 |
| 7.0 | 2.4 |
| 7.4 | 2 |
| 7.8 | 1 |

The above results in Tables 3 and 4 indicate that there is a rapid fall-off in stability of esters of pyroglutamic acid with increasing pH value. Ideally, compositions according to the invention should be shelf stable for at least one year, which involves selection of a suitable pH value to enable the chosen esters of pyroglutamic acid to have a half-life of at least one year.

EXAMPLES OF THE INVENTION

The following clinical studies illustrate the treatment of skin disorders with therapeutical compositions according to the invention.

EXAMPLE 1

This example illustrates the treatment of ichthyosis vulgaris.

20 patients suffering from ichthyosis vulgaris primarily involving the arms, some with atopic eczema, are to be treated with a cream containing 2% by weight of pyroglutamic acid ethyl ester.

In order to establish efficacy of the pharmaceutical composition according to the invention, the clinical test should take the form of a comparison with an appropriate placebo and a commercially available product containing 10% by weight of urea, specifically prescribed for the treatment of ichthyosis, hyperkeratosis and other chronic skin conditions. This commercially available product should be designated the "control", whereas the cream containing 2% by weight of pyroglutamic acid ethyl ester (pH 3.8) should be the "test" cream, but should not contain pyroglutamic acid ethyl ester.

The clinical trial should be carried out by a consultant dermatologist as a double blind trial, each patient using the test or control creams twice daily, the cream being applied to the area of the arms affected by this skin disorder.

The clinical study should last for a total of 4 weeks, after which the results should be assessed by the consultant dermatologist. It will be shown that the test cream produces an improvement in the condition of the skin of each patient, as compared with the placebo cream. Furthermore, the "test" cream will be more cosmetically acceptable than the control cream, and will result in fewer complaints from the subjects being treated.

These data will clearly demonstrate that the therapeutical composition according to the invention containing 2% by weight pyroglutamic acid ester is efficacious and, furthermore, preferred by the patient to a widely used commercially available pharmaceutical preparation, containing 10% by weight urea, prescribed for the treatment of ichthyosis vulgaris.

EXAMPLE 2

This example illustrates the treatment of acne.

Forty patients suffering from moderate acne are to be treated with a cream containing 5% by weight pyroglutamic acid ethyl ester.

In order to demonstrate the significant beneficial efficacy of the pharmaceutical composition according to the invention, the clinical study should compare this composition with an appropriate placebo (without pyroglutamic acid ethyl ester) and an other commercially available product specifically prescribed for the treatment of acne.

The clinical study should be performed by a consultant dermatologist and maintained as a double blind trial. Each patient should apply the designated test material twice daily for 3 months to the affected area.

Upon completion of the treatment period, the areas treated with the 5% by weight pyroglutamic acid ethyl ester cream will exhibit a clinically significant decrease in the severity of acne as compared to placebo treatment. Furthermore, the pyroglutamic acid ethyl ester treated subjects will exhibit less severe side effects and complaints as compared to some other commercially available treaments.

EXAMPLE 3

This example illustrates the treatment of xerosis.

Thirty patients suffering from moderate xerosis are to be treated with a cream containing 2% by weight pyrogutamic acid ethyl ester.

In order to demonstrate the significant beneficial efficacy of the pharmaceutical composition according to the invention, the clinical study should compare this composition with a "placebo" which does not contain pyroglutamic acid ethyl ester.

The clinical study should be performed by a consultant dermatologist and maintained as a double blind trial. Each patient should apply the designated test material twice daily for 1 month to the affected area.

Upon completion of the treatment period, the areas treated with a 2% pyroglutamic acid ethyl ester cream will exhibit a clinically significant decrease in the severity of xerosis as compared to placebo treatment.

What is claimed is:

1. A method for the treatment of a skin disorder in man and other mammals selected from the group consisting of:
   Ichthyosiform dermatoses,
   Conradi's syndrome,
   Localised hyperkeratotic conditions,
   Dandruff,
   Callous-forming disorders,
   Psoriasis,
   Eczema,
   Xerosis,
   Warts,
   Dermatomycoses,
   Pityriasis rosea and Pityriasis alba,
   Lichen planus and Lichen simplex chronicus,
   Cicatricial alopecia with dry flaky scalp,
   Darier's disease,
   Pruritus,
   Seborrhoeic dermatitis,
   Seborrhoeic eczema,
   Acne, and
   Scabies,
said method comprising applying to involved areas of the body a composition comprising:
   (i) an effective amount of an ester of pyroglutamic acid having the structure:

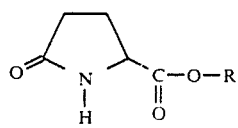

where
R is a group:

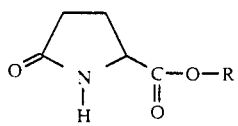

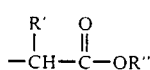

where
R' and R" are the same or different and are each represented by H or the group:

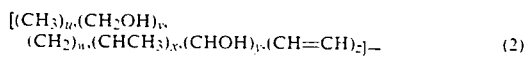

where either
u or v is 1 and the other of them is zero
w is zero, or an integer of from 1 to 21
x is zero, or an integer of from 1 to 4
y is zero, or an integer of from 1 to 2
z is zero, or an integer of from 1 to 4; and
u+v+w+x+y+z is an integer of from 1 to 22
the subgroups within the group (2) being in any sequence provided that when the subgroup (CH=CH) is present, then the total number of carbon atoms in said group (2) will be from 10 to 22; and
   (ii) a therapeutically acceptable vehicle for the ester.

2. The method of claim 1, wherein the Ichthyosiform dermatoses are:
   Ichthyosis vulgaris,
   Sex-linked ichthyosis, or
   Epidermolytic ichthyosis.

3. The method of claim 1, wherein the localised hyperkeratolytic conditions are:
   Keratosis pilaris,
   Keratosis punctata,
   Keratosis senilis, or
   Keratosis striata.

4. The method of claim 1, wherein the callous-forming disorders are:
   Palmar and Plantar hyperkeratosis, Corns, or Palmar and Plantar keratoderma.

5. The method of claim 1, wherein the warts are:

Keratotic warts, warts associated with Herpes,

Keratoacanthoma or

Warty naevus.

6. The method of claim 1, wherein the Dermatomyces is Tinea pedis.

7. The method of claim 1, wherein the ester of pyroglumatic acid is selected from the group consisting of:

2-[pyroglutamoyloxy]-propionic acid,
methyl-2-[pyroglutamoyloxy]-acetate,
ethyl-2-[pyroglutamoyloxy]-propionate,
ethyl-2-[pyroglutamoyloxy]-n-butyrate,
ethyl-2-[pyroglutamoyloxy]-n-iso-butyrate,
ethyl-2-[pyroglutamoyloxy]-n-valerate,
ethyl-2-[pyroglutamoyloxy]-n-caproate,
ethyl-2-[pyroglutamoyloxy]-n-heptylate,
ethyl-2-[pyroglutamoyloxy]-n-caprylate,
ethyl-2-[pyroglutamoyloxy]-n-perlargonate,
ethyl-2-[pyroglutamoyloxy]-3-hydroxybutyrate,
iso-propyl-2-[pyroglutamoyloxy]-propionate,
iso-propyl-2-[pyroglutamoyloxy]-n-caprylate,
n-propyl-2-[pyroglutamoyloxy]-n-propionate,
n-propyl-2-[pyroglutamoyloxy]-n-caprylate,
lauryl-2-[pyroglutamoyloxy]-n-caprylate,
stearyl-2-[pyroglutamoyloxy]-n-caprylate,
stearyl-2-[pyroglutamoyloxy]-propionate,
12-hydroxystearyl-1-[pyroglutamoyloxy]-n-propionate,
stearyl-2-[pyroglutamoyloxy]-stearate,
palmityl-2-[pyroglutamoyloxy]-n-propionate,
linoleyl-2-[pyroglutamoyloxy]-n-propionate,
linoleyl-2-[pyroglutamoyloxy]-n-caprylate,
glyceryl mono(2-[pyroglutamoyloxy]-n-propionate),
glyceryl mono(2-[pyroglutamoyloxy]-n-caprylate),
glyceryl di(2-[pyroglutamoyloxy]-n-propionate), and mixtures thereof.

* * * * *

UNITED STATES PATENT AND TRADEMARK OFFICE
CERTIFICATE OF CORRECTION

PATENT NO. : 5,045,559

DATED : September 3, 1991

INVENTOR(S) : Scott

It is certified that error appears in the above-identified patent and that said Letters Patent is hereby corrected as shown below:

Claim 1, column 12, lines 25 to 30, delete formula.

Signed and Sealed this

Twentieth Day of April, 1993

Attest:

MICHAEL K. KIRK

*Attesting Officer*　　　Acting Commissioner of Patents and Trademarks